(12) United States Patent

Galimberti et al.

(10) Patent No.: US 6,852,884 B2
(45) Date of Patent: Feb. 8, 2005

(54) PROCESS FOR PREPARING ACYLFLUORIDES

(75) Inventors: Marco Galimberti, Milan (IT); Walter Navarrini, Milan (IT)

(73) Assignee: Solvay Solexis S.p.A., Milan (IT)

( * ) Notice: Subject to any disclaimer, the term of this patent is extended or adjusted under 35 U.S.C. 154(b) by 0 days.

(21) Appl. No.: 10/461,349

(22) Filed: Jun. 16, 2003

(65) Prior Publication Data

US 2003/0236436 A1 Dec. 25, 2003

(30) Foreign Application Priority Data

Jun. 21, 2002 (IT) ...................... MI2002A1365

(51) Int. Cl.$^7$ .......................... C07C 51/58; C07C 59/00; C07C 53/38
(52) U.S. Cl. ...................... 562/840; 562/843; 562/849; 562/853
(58) Field of Search ................. 562/840, 843, 562/849, 853

(56) References Cited

U.S. PATENT DOCUMENTS 3,113,967 A   12/1963  Fawcett ..................... 260/544
3,114,778 A   12/1963  Fritz et al. .................. 260/614
3,758,538 A  * 9/1973  Litt et al. .................... 556/113
4,769,184 A  * 9/1988  Okabe et al. ................ 562/849
6,013,795 A    1/2000  Manzara et al. ............. 544/106

* cited by examiner

Primary Examiner—Johann Richter
Assistant Examiner—Sikarl A. Witherspoon
(74) Attorney, Agent, or Firm—Arent Fox PLLC

(57) ABSTRACT

A process for preparing acylfluorides by reaction of carbonyl fluoride $COF_2$ with compounds having general formula:

$$T=CR_1R_2 \qquad (I)$$

wherein:

T is O or $CF_2$ $R_1$ and $R_2$, equal or different, are F or a $R(O)_t$ radical, wherein R=linear or branched $C_1$–$C_7$ (per)fluoroalkyl, optionally containing one or more oxygen atoms, t is an integer equal to zero or 1;

wherein a catalyst supported on porous compound is used, the catalyst being selected from: CsF, RbF, KF, AgF, each optionally in admixture with one or more of the others.

13 Claims, No Drawings

PROCESS FOR PREPARING ACYLFLUORIDES

The present invention relates to a process for obtaining acylfluorides with improved yields and selectivity.

Processes for obtaining acylfluorides are known in the prior art. In U.S. Pat. No. 3,113,967 it is described the acylfluoride synthesis by condensation between $COF_2$ and linear and cyclic fluoroolefins. The catalyst is selected from non oxidizing fluoride salts capable to make available the ion fluoride. Among cations, those of the elements of the first group are mentioned and, besides, iron, cobalt, nickel, zinc, tin, bismuth, tetralkylammonium, trialkylammonium. In said patent it is mentioned that in the reaction the use of the solvent in combination with the metal fluoride is necessary to obtain high yields. In the Examples of said patent it is shown that in absence of solvent, the fluoroolefin being equal, the yields are lower. It is known that to obtain acylhalides it is necessary to operate in anhydrous environment. Therefore the used solvents must be treated to remove as much as possible the water traces. From an industrial point of view, the use of anhydrous solvents requires supplementary units and makes it harder to isolate the product from the reaction environment.

U.S. Pat. No. 3,114,778 describes the synthesis of perfluorinated vinylethers, wherein in the first step perfluorinated acylfluorides are reacted with hexafluoropropylen oxide (HFPO), in the presence of a catalyst formed by an alkaline metal fluoride, such for example CsF, in combination with an inert polar solvent. The reaction to obtain acylfluorides shows the same drawbacks mentioned above for the previous patent.

In U.S. Pat. No. 6,013,795 fluoroalkylcarbonyl compounds alpha branched to the carbonyl group are described. Said compounds, preferably having at least 8 carbon atoms, are synthesized by fluorination with $F_2$, or by electrochemical route with HF in the presence of KF of the corresponding hydrogenated alkylcarbonyl compounds. In the patent it is mentioned that the yields for the electrochemical fluorination reaction are at most 50%, while for the direct fluorination reaction they are comprised between 60% and 80%. In this case there is however the drawback of a high fluorine consumption, which as known is an expensive reactant and is to be cautiously used. Besides it is known that both the above processes lead to the formation of various by-products making them not optimal from the industrial point of view.

The need was felt to have available a process for obtaining by direct synthesis, also starting from (per)fluoroolefins, acylfluorides with improved yields and selectivity, even by continuously operating.

The Applicant has surprisingly and unexpectedly found that by using the process described hereinafter it is possible to solve the above technical problem, and therefore to have available a simplified industrial process capable to operate even continuously, through which it is possible to obtain acylfluorides with improved yields and selectivity.

An object of the present invention is a process for preparing acylfluorides by reaction of carbonyl fluoride ($COF_2$) with compounds having general formula:

$$T=CR_1R_2 \quad (I)$$

wherein:

T is O or $CF_2$ $R_1$ and $R_2$, equal or different, are F or a $R(O)_t$ radical, with the proviso that:
when $T=CF_2$, then:
R=linear or branched $C_1–C_7$ (per) fluoroalkyl, preferably $C_1–C_5$, optionally containing one or more oxygen atoms, t is an integer equal to zero or 1;

when T is oxygen, then:
$R_1$ and $R_2$ are equal to each other and have the meaning of R=$C_1–C_7$ (per)fluoroalkyl, optionally containing one or more oxygen atoms, with t=0;

wherein a catalyst supported on porous compound is used, the catalyst being selected from:

CsF, RbF, KF, AgF, each optionally in admixture with one or more of the others, wherein the porous compound is formed by a compound inert under the reaction conditions and has a porosity, determined by the mercury-helium method, and expressed as ratio between the pore volume and the total solid volume, higher than 0.2, preferably higher than 0.3.

The formula (I) compounds are known compounds.

The ratio by moles between $COF_2$ and the formula (I) compounds ranges from 1:1 to 6:1.

Preferably the porous compound which forms the catalyst support is constituted by one or more fluorides selected from one or more of the following groups:

alkaline metal fluorides, preferably LiF and NaF;
alkaline-earth metal fluorides, preferably the following: $CaF_2$, $BaF_2$, $MgF_2$, $SrF_2$;
AgF.

When the porous support is formed by one or more fluorides indicated as catalysts, the porous support forms the catalyst. On the porous support one or more of the above mentioned catalysts can be supported.

The condensation reaction between the compounds of formula (I) and $COF_2$ according to the present invention is carried out at a temperature in the range 100° C.–400° C., preferably 150° C.–300° C.

Preferably the reaction is carried out in gaseous phase.

The conversion of the formula (I) compound in the process according to the present invention is generally very high, even higher than 90% and the selectivity always remains very high, even when the conversion of the formula (I) compound is not complete.

An advantage of the process according to the present invention is that by starting from (per)fluoroolefins of formula (I) the main by-product is a (per)fluoroketone; when the (per)fluoroketone is among the compounds defined in formula (I) with T=oxygen, it can be used in the reaction according to the present invention and therefore it is possible to increase the total yields in acylfluoride. See the Examples.

The process of the present invention can be carried out in a continuous way or in batch.

The pressure at which one operates is generally that atmospheric and it is anyway possible to operate also at higher pressures, for example up to 40 Atm (4.05.10$^6$ Pa).

When compounds of formula (I) having boiling point higher than or equal to the room temperature are used, it is possible to dilute the reactants with an inert gas, for example nitrogen, helium.

In this case it is possible to use as diluent, alternatively to the above described inert gases, also an inert perfluorocarbon or a perfluoroether, at the vapour state under the reaction conditions, such for example $C_3F_8$, $C_2F_6$, cyclo-$C_4F_8$, $C_4F_{10}$.

The contact times in the continuous process are comprised between 2 seconds and 1 minute, depending on the reactor shape and the reactant flows.

When the porous support is formed by one or more fluorides selected from the above groups, it is preferably obtainable starting from the corresponding acid fluorides and heating at a temperature in the range 450° C.–550° C. in an inert gas flow, so to obtain the substantial removal of the hydrofluoric acid.

The catalyst is deposited on the porous support by impregnating the latter with a solution containing dissolved the metal fluoride catalyst and removing the solvent by heating in inert gas flow or by evaporation at reduced pressure. The solvent must not solubilize the porous support. Preferably the solutions containing the catalyst are based on alcohols, preferably methanol. Mixtures of alcohols with other solvents can be used with the proviso that they do not solubilize the porous support.

The skilled man in the field is capable to prepare said mixtures knowing the metal fluoride used to prepare the support and that to be used as catalyst.

The concentration by weight of the metal fluoride as catalyst which is supported can range from 1% up to 40% by weight and more, preferably from 10 to 30% by weight.

The preferred supported catalyst uses as catalyst CsF and as a support NaF.

The catalyst has a particle size suitable for a fixed or a fluidized bed. In the case of a fixed bed generally the minimum particle size must not be lower than 0.05 mm. The feasible sizes depend on the catalyst support compound shape, for example, spheres, cylinders or granules.

As said, the present invention catalyst is used in the reactions between the formula (I) compounds, preferably (per)fluoroolefins, and $COF_2$.

As said, the acylfluoride reaction products are obtained with improved yields and selectivity.

With the term "yield" it is meant the ratio (expressed in percentage) between the obtained acylfluorides moles and the theoretically obtainable moles according to the reaction stoichiometry in the case of complete conversion to acylfluoride of the limiting reactant.

With the term "selectivity" it is meant the ratio (expressed in percentage) between the obtained acylfluoride moles and those theoretically obtainable, according to the reaction stoichiometry, calculated on the reactant moles really converted during the reaction.

The catalyst activity is maintained for long periods, for example even over one year, and ratios between the converted moles of the formula (I) compound and the catalyst moles higher than 100, are reached.

A further process advantage according to the present invention is that one can operate in absence of solvent.

If desired, one can operate in the presence of a dipolar aprotic solvent, for example mono- or poly-glyme, acetonitrile, DMF.

In this case the invention process can be carried out even at lower tempertures. Generally the solvent amounts are equal to or lower than the weight of the used supported catalyst.

The aylfluorides obtainable by the invention process have the following general formula:

$$(R')COF \quad (II)$$

wherein:

$R'=CF_3R_1R_2C$ wherein $R_1$ and $R_2$ are as defined in the formula (I) compound when $T=CF_2$, or $R'=R_1=R_2$ as above defined in the formula (I) compound when T is oxygen.

The following Examples illustrate the invention without limiting the scope thereof.

EXAMPLES

Example 1

Catalyst Preparation 25 g of $NaHF_2$ sodium acid fluoride are slowly heated in a nitrogen flow of 2 liters/h up to the temperature of 500° C., and maintained under these conditions for about one hour, until HF results almost completely removed from the support. 16 g of NaF with a porosity equal to 0.40 are obtained. The support is then charged in a rotating evaporator and degassed under vacuum at room temperature. Then a solution of 5 g of CsF dissolved in 10 cc of methyl alcohol is then sucked in the evaporator to impregnate the support and then drying under vacuum is continued at the temperature of 80°–90° C.

The so prepared catalyst is introduced into the used reactor and dried in an inert gas flow at the temperature of 200°–250° C. for two hours before being used. The catalyst porosity is 0.38.

Example 2

Synthesis in a Continuous Way of perfluoroisobutyryl fluoride $(CF_3)_2CFCOF$ 434 g of CsF catalyst supported on NaF prepared as described in the Example 1 are introduced in a 270 $cm^3$ tubular reactor having the diameter of 2.5 cm. They are then activated by heating at 200° C. in He flow. Such catalyst is then saturated with a $COF_2$ flow at the temperature of 190° C.

The acylfluoride synthesis is carried out by flowing on the catalytic bed a flow of 2.0 liters/h (l/h) of $COF_2$ (obtained by direct reaction between 2.0 l/h of CO and 2.1 l/h of $F_2$) and 1.75 liters/h of perfluoropropene $C_3F_6$. The reaction progress is followed by analyzing by GC and IR analyses the gases flowing out from the reactor; once the balance is reached, the product is conveyed to a storing bottle maintained at −196° C. After distillation in vacuum ramp at $10^{-3}$ mbar (0.1 Pa), the acylfluoride is recovered with a yield and selectivity of 95%.

Example 3

Synthesis in a Continuous Way of perfluoro-2 methoxy-propionyl fluoride $(CF_3)(CF_3O)CFCOF$ The same reactor used in the Example 2, containing the same activated catalyst, is washed with a $COF_2$ flow at the temperature of 210° C.

The acylfluoride synthesis is carried out by flowing on the catalytic bed, maintained at 210° C., a flow of 2.0 l/h of $COF_2$ (obtained by direct reaction between 2.2 l/h of CO and 2.0 l/h of $F_2$) and 1.25 l/h of perfluoro-methylvinylether $CF_2=CR-O-CF_3$. The reaction progress is followed by analyzing by GC and IR analyses the gases flowing out from the reactor; once the balance is reached, the product is conveyed to a storing bottle maintained at −196° C. After distillation in vacuum ramp at $10^{-3}$ mbar, the acylfluoride is recovered with a yield and selectivity of 93%.
Characterization $(CF_3)(CF_3O)CFCOF$ Boiling point at atmospheric pressure: 10° C.
Experimental curve of the vapour tension (P in mbar and T in K): ln (P)=19.697-3620.4/T.
$^{19}F$ NMR spectrum in ppm ($CFCl_3=0$) : 26.7 (1F, —COF); −56.5 (3F, —$OCF_3$); −82.4 (3F, —$CF_3$) ; −132.7 (1F, CF).

Mass spectrum (electronic impact): main peaks and relative intensities: 31(25), 47(30), 69(100), 98(47), 119(78), 147(9), 185(25).

IR spectrum ($cm^{-1}$) (intensity: w=weak, m=mean, s=strong, vs=very strong): 1888(s), 1338(w), 1294(vs), 1248 (vs), 1159(vs), 1225(s), 1015(s), 899(w), 699(w).

Example 4

Synthesis in a Continuous Way of perfluoropropionyl fluoride $CF_3CF_2COF$

The same reactor used in the Example 3, containing the activated catalyst of Example 2, is washed with a $COF_2$ flow at the temperature of 250° C.

The acylfluoride synthesis is carried out by flowing on the catalytic bed, maintained at 250° C., a flow of 2.0 l/h of $COF_2$ (obtained by direct reaction between 2.2 l/h of CO and 2.0 l/h of $F_2$) and 1.0 l/h of tetrafluoro-ethylene inhibited with β-terpene. The reaction progress is followed by analyzing by GC and IR analyses the gases flowing out from the reactor; once the balance is reached, the product is conveyed to a storing bottle maintained at −196° C. After distillation in vacuum ramp at $10^{-3}$ mbar (0.1 Pa), the acylfluoride is recovered with a yield and selectivity of 68%. The main by-product is the $C_2F_5COC_2F_5$ ketone.

Example 5

Synthesis in Batch of perfluoro-2,2-dimethoxy propionyl fluoride $(CF_3)$ $(CF_3O)_2CCOF$ 240 mmoles of $COF_2$ and 192 mmoles of perfluoro-1,1-dimethoxyethylene $(CF_3O)_2C=CF_2$ are condensed in a 325 ml reactor equipped with manometer, containing 30 g of supported catalyst prepared as described in the Example 1, activated by heating at 200° C. under vacuum at $10^{-3}$ mbar (0.1 Pa) for 2 hours. The whole is heated at 190° C. for 40 hours and then at 200° C. for 43 hours, until the internal pressure stabilizes. At this point the reaction does not further proceed and then one proceeds to recover the product by successive distillations in vacuum ramp at $10^{-3}$ mbar (0.1 Pa) through three traps, cooled respectively at −65° C., −110° C. and −196° C. The acylfluoride $(CF_3)$ $(CF_3O)_2$CCOF is isolated in the trap at −65° C. with a 60% yield and a 78% selectivity. The other component of the reacted mixture is the starting olefin.

Characterization $(CF_3)$ $(CF_3O)_2$CCOF

Boiling point at atmospheric pressure: 41° C.
Experimental curve of the vapour tension (P in mbar and T in K): ln (P)=18.928-3769.6/T.
$^{19}F$ NMR spectrum in ppm ($CFCl_3$=0): 26 (1F, —COF); −59.6 (6F, —$OCF_3$); −81.8 (3F, —$CF_3$)
Mass spectrum (electronic impact): main peaks and relative intensities: 47(3), 69(100), 97(6), 167(2), 232(2), 251 (1).
IR spectrum (cm$^{-1}$) (intensity: w=weak, m=mean, s=strong, vs=very strong): 1885(s), 1292(vs), 1258(vs), 1159(m), 1227(s), 1015(m), 890(w).

Example 6

Synthesis in Batch of perfluoroisobutyryl fluoride $(CF_3)_2$CFCOF by Retrocondensation of perfluoro (bis-isobutyl)ketone $(CF_3)_2$CFCOCF$(CF_3)_2$ The same reactor of Example 5 is used for this reaction; the catalyst, CsF supported on NaF (Example 1), is activated by heating at 200° C. under vacuum at $10^{-3}$ mbar ($10^{-2}$ Pa) for 4 hours. 59 mmoles of $COF_2$ and 12 mmoles of $(CF_3)_2$CFCOCF$(CF_3)_2$ are then condensed. It is heated at 250° C. for 5 hours and then one proceeds to recover the product by successive distillations in vacuum ramp at $10^{-3}$ mbar through three traps cooled respectively at −50° C., −110° C. and −196° C.

23.6 mmoles of acylfluoride $(CF_3)_2$CFCOF are isolated in the trap at −110° C. with a yield and selectivity of 98%.

Example 7 (Comparative)

Synthesis of $(CF_3)_2$CFCOF in a Continuous Way Using as Catalyst Unsupported CsF 87 g of CsF in powder are introduced into a tubular reactor equal to that of the Example 2. They are then activated as described in the Example 2.

By repeating the reaction on pefluoropropene as described in the Example 2, by gaschromatographic analysis it is found that the perfluoropropene conversion to acylfluoride is of 15%.

Example 8

Synthesis of $(CF_3)_2$CFCOF in Batch Using as Catalyst Supported CsF 7.74 g of supported catalyst (corresponding to 10 mmoles of CsF) which are activated by heating at 300° C. under vacuum ($10^{-3}$ mbar) for three hours are introduced into a 150 ml autoclave equipped with pressure transducer. Then 60 mmoles of perfluoropropene and 80 mmoles of $COF_2$ are condensed in the autoclave. The system is heated at the reaction temperature of 190° C. The pressure reduction is followed in the time.

After 14 hours the heating is turned off and the autoclave content is transferred into a vacuum ramp.

By distillation under vacuum at $10^{-3}$ mbar ($10^2$ Pa) the acylfluoride $(CF_3)_2$CFCOF is recovered. The yield is 77% and the selectivity is 81%. The main reaction by-product is the $C_3F_7COC_3F_7$ ketone (yield 10%)

Example 9 (Comparative)

Synthesis of $(CF_3)_2$CFCOF in Batch by Using as Catalyst Unsupported CsF

Example 8 is repeated using CsF in powder at the place of the supported catalyst, in the same amount (10 mmoles). The yield of $(CF_3)_2$CFCOF is 10%.

What is claimed is:

1. A process for preparing acylfluorides by reaction of carbonyl fluoride $COF_2$ with a compound having general formula $$T=CR_1R_2 \quad (I)$$

wherein:

T is O or $CF_2$ $R_1$ and $R_2$, equal or different, are F or a $R(O)_t$ radical, with the proviso that:
when T=$CF_2$, then:
R=linear or branched $C_1$–$C_7$ (per)fluoroalkyl, optionally containing one or more oxygen atoms,
t is an integer equal to zero or 1;
when T is oxygen, then:
$R_1$ and $R_2$ are equal to each other and have the meaning of
R=$C_1$–$C_7$ (per)fluoroalkyl, optionally containing one or more oxygen atoms, with t=0;
wherein a catalyst supported on porous compound is used, the catalyst being selected from:
CsF, RbF, KF, AgF, each optionally in admixture with one or more of the others, wherein the porous compound is formed by a compound inert under the reaction conditions and has a porosity, determined by the mercury-helium method, and expressed as ratio between the pore volume and the total solid volume, higher than 0.2
wherein said process is conducted in the absence of a solvent.

2. A process according to claim 1, wherein the ratio by moles between $COF_2$ and the formula (I) compounds ranges from 1:1 to 6:1.

3. A process according to claim 1, wherein the porous compound which forms the catalyst support is constituted by one or more fluorides selected from one or more of the following groups:
alkaline metal fluorides;
alkaline-earth metal fluorides;
AgF.

4. A process according to claim 1, wherein when the porous support is constituted by one or more fluorides indicated as catalysts, the porous support constitutes I the catalyst.

5. A process according to claim 1, wherein the temperature is in the range 100° C.–400° C.

6. A process according to claim 1, carried out in gaseous phase.

7. A process according to claim 1, carried out in a continuous way or in batch.

8. A process according to claim 1, wherein the used pressure ranges from the atmospheric pressure to 40 Atm ($4.05 \cdot 10^6$ Pa).

9. A process according to claim 2, wherein inert gases are used as diluents, or perfluorocarbons or perfluoroethers.

10. A process according to claim 7, continuously carried out wherein the contact times are comprised between 2 seconds and 1 minute.

11. A process according to claim 1, wherein the concentration by weight of the metal fluoride catalyst which is supported ranges from 1% up to 40% by weight.

12. A process according to claim 1, wherein the catalyst is CsF supported on NaF.

13. A process according to claim 1, wherein one operates in the presence of a dipolar aprotic solvent, in an amount by weight equal to or lower than the weight of the used catalyst.

* * * * *